United States Patent
Jones et al.

(10) Patent No.: US 11,783,927 B2
(45) Date of Patent: Oct. 10, 2023

(54) METHODS AND SYSTEMS FOR CALCULATING HEALTH CARE TREATMENT STATISTICS

(71) Applicant: HEALTHSPARQ, INC., Portland, OR (US)

(72) Inventors: Matthew Jones, Poulsbo, WA (US); Keith Lomurray, Salt Lake City, UT (US)

(73) Assignee: HEALTHSPARQ, INC., Portland, OR (US)

( * ) Notice: Subject to any disclaimer, the term of this patent is extended or adjusted under 35 U.S.C. 154(b) by 1182 days.

(21) Appl. No.: 14/937,755

(22) Filed: Nov. 10, 2015

(65) Prior Publication Data

US 2016/0132646 A1    May 12, 2016

Related U.S. Application Data

(60) Provisional application No. 62/078,327, filed on Nov. 11, 2014.

(51) Int. Cl.
*G16H 15/00* (2018.01)
*G16H 70/00* (2018.01)
*G06Q 10/10* (2023.01)
*G06Q 40/08* (2012.01)

(52) U.S. Cl.
CPC ............ *G16H 15/00* (2018.01); *G06Q 10/10* (2013.01); *G06Q 40/08* (2013.01); *G16H 70/00* (2018.01)

(58) Field of Classification Search
CPC combination set(s) only.
See application file for complete search history.

(56) References Cited

U.S. PATENT DOCUMENTS

| | | | |
|---|---|---|---|
| 7,003,472 B2 * | 2/2006 | Sachdeva | |
| 7,493,266 B2 | 2/2009 | Gupta | |
| 7,739,128 B2 | 6/2010 | Farris | |
| 7,792,687 B2 | 9/2010 | Farris | |
| 7,890,356 B1 * | 2/2011 | Drucker et al. | |
| 7,979,286 B2 | 7/2011 | Manning et al. | |
| 8,019,627 B2 | 9/2011 | Baylor et al. | |
| 8,069,080 B2 | 11/2011 | Rastogi | |
| 8,498,885 B2 | 7/2013 | Vanderzee et al. | |
| 8,510,124 B2 | 8/2013 | Gowdy et al. | |

(Continued)

*Primary Examiner* — Michael Tomaszewski
*Assistant Examiner* — William T. Monticello
(74) *Attorney, Agent, or Firm* — BLUESHIFT IP, LLC; Cynthia Gilbert

(57) ABSTRACT

Systems and methods for calculating health care treatment statistics are provided. In one embodiment, a system comprises a data-holding subsystem storing raw medical claims data in non-transitory memory, and a logic subsystem configured to partition the raw medical claims data into a plurality of data sets based on one or more of insurance type, episode grouping, member key, date-of-service key, or a combination thereof, wherein the logic subsystem is further configured to calculate statistics based on each of the plurality of data sets and output correlated calculation results for display on a user device, and wherein the statistics include a frequency of patients receiving a health care service and an average cost of the health care service. In this way, a health care consumer may know what to expect for different treatment options for a given medical condition.

20 Claims, 10 Drawing Sheets

(56) References Cited

U.S. PATENT DOCUMENTS

| | | |
|---|---|---|
| 9,123,072 B2 | 9/2015 | Ketchel, III |
| 9,798,888 B2 * | 10/2017 | Beiter et al. |
| 9,996,666 B1 * | 6/2018 | Wilson et al. |
| 2008/0275737 A1 * | 11/2008 | Gentry et al. |
| 2009/0198517 A1 * | 8/2009 | Ruben et al. |
| 2010/0010828 A1 | 1/2010 | Gupta |
| 2010/0094660 A1 * | 4/2010 | Michalowski et al. |
| 2011/0022479 A1 * | 1/2011 | Henley |
| 2011/0071854 A1 | 3/2011 | Medeiros et al. |
| 2011/0252275 A1 * | 10/2011 | Gudlavenkatasiva et al. |
| 2011/0270632 A1 | 11/2011 | Manning et al. |
| 2012/0054119 A1 | 3/2012 | Zecchini |
| 2012/0182939 A1 | 7/2012 | Rajan et al. |
| 2012/0232936 A1 | 9/2012 | Bravata et al. |
| 2012/0259654 A1 | 10/2012 | Vanderzee et al. |
| 2012/0259662 A1 | 10/2012 | Vanderzee et al. |
| 2013/0090948 A1 | 4/2013 | Upadhyayula et al. |
| 2013/0291060 A1 * | 10/2013 | Moore |
| 2014/0108042 A1 * | 4/2014 | Reddy et al. |
| 2014/0257047 A1 * | 9/2014 | Sillay et al. |
| 2015/0294338 A1 | 10/2015 | Ketchel, III et al. |
| 2015/0317337 A1 * | 11/2015 | Edgar |
| 2015/0379430 A1 * | 12/2015 | Dirac et al. |
| 2016/0011911 A1 * | 1/2016 | Rangaraju et al. |

* cited by examiner

METHODS AND SYSTEMS FOR CALCULATING HEALTH CARE TREATMENT STATISTICS

CROSS REFERENCE TO RELATED APPLICATIONS

The present application claims priority to U.S. Provisional Patent Application No. 62/078,327, entitled "METHODS AND SYSTEMS FOR CALCULATING HEALTH CARE TREATMENT STATISTICS," and filed on Nov. 11, 2014, the entire contents of which are hereby incorporated by reference for all purposes.

BACKGROUND AND SUMMARY

Healthcare in the United States is the most expensive in the world and is regularly ranked last among similar countries for the quality of healthcare. Over $8,000 per capita on healthcare services in the United States in 2011. Most of the time, consumers do not have any idea how much their healthcare may cost prior to treatment. Consumers are not encouraged to compare costs for treatments and services and they are not encouraged to look for referral options. The cost for treatments and services varies widely from doctor to doctor and from facility to facility. For example, prices for common services, such as MRIs, can vary by thousands of dollars across different regions of the country, within the same metro areas, and even across hospitals and clinics that share the same healthcare providers.

This inefficiency contributes to the overall rise of costs within the healthcare industry. In 2011, health expenditures in the United States reached $2.7 trillion, more than ten times the $256 billion spent in 1980. Furthermore, national health spending is expected to grow faster than the national income for the foreseeable future.

The inventors have recognized the above issues and have devised several approaches to address them. In particular, systems and methods for calculating health care treatment statistics are provided. In one embodiment, a system comprises a data-holding subsystem configured to hold raw medical claims data in non-transitory memory, and a logic subsystem configured to partition the raw medical claims data into a plurality of data sets based on one or more of insurance type, episode grouping, member key, date-of-service key, or a combination thereof, wherein the logic subsystem is further configured to calculate statistics based on each of the plurality of data sets and output correlated calculation results for display on a user device, wherein the statistics include a frequency of patients receiving a health care service and an average cost of the health care service.

In another embodiment, a method comprises partitioning raw claims data into a plurality of data sets and calculating statistics based on the plurality of data sets regarding treatment options and health care services. Statistics may include unit costs of the treatment options and health care services including the facility costs, and a probability that a user will receive a health care service. The computing device may aggregate and format the results to provide users with a clear overview of treatment options, including typical timeframes for treatment and the total cost of the treatment. The overview may further include service options and indicate place-of-service savings to the user. In this way, a health care consumer may know what to expect for different treatment options for a given medical condition, including cost, timeframe, and the percentage of consumers who receive particular services during a treatment.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The present description relates to systems and methods of healthcare transparency. In particular, systems and methods for estimating health care treatment costs are provided.

Figure 1:
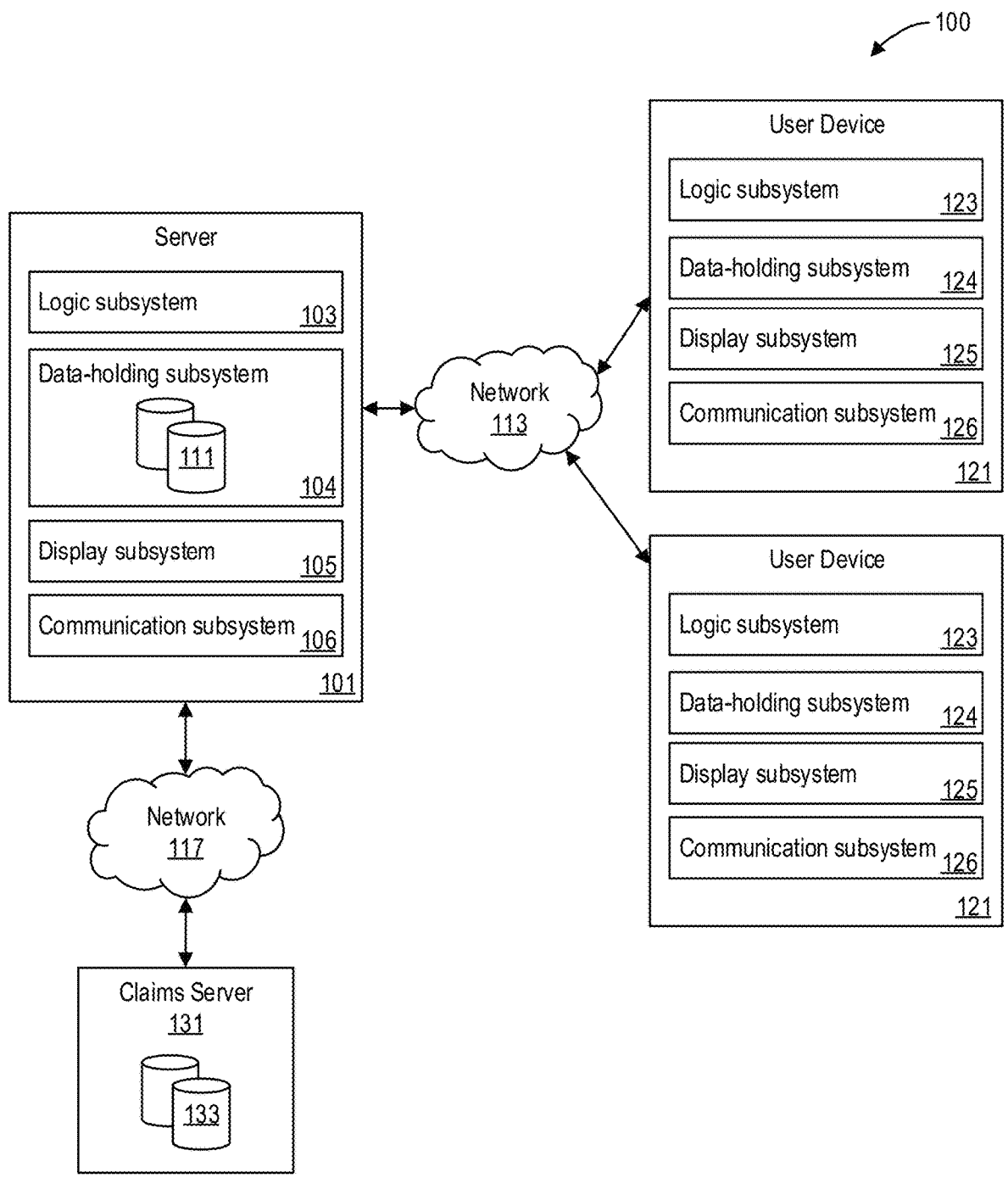
FIG. 1 illustrates an overview of an exemplary computing environment according to an embodiment.

FIG. 1 illustrates an example computing environment 100 in accordance with the current disclosure. In particular, computing environment 100 includes a server 101, a plurality of user devices or client systems 121, a claims server 131, and networks 113 and 117. However, not all of the components illustrated may be required to practice the invention. Variations in the arrangement and type of the components may be made without departing from the spirit or scope of the invention.

Server 101 may be a computing device configured to calculate health care treatment costs from claims data. In different embodiments, server 101 may take the form of a mainframe computer, server computer, desktop computer, laptop computer, tablet computer, home entertainment computer, network computing device, mobile computing device, mobile communication device, gaming device, etc.

Server 101 includes a logic subsystem 103 and a data-holding subsystem 104. Server 101 may optionally include a display subsystem 105, communication subsystem 106, and/or other components not shown in FIG. 1. For example, server 101 may also optionally include user input devices such as keyboards, mice, game controllers, cameras, microphones, and/or touch screens.

Logic subsystem 103 may include one or more physical devices configured to execute one or more instructions. For example, logic subsystem 103 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 103 may include one or more processors that are configured to execute software instructions. Additionally or alternatively, the logic subsystem 103 may include one or more hardware or firmware logic machines configured to execute hardware or firmware instructions. Processors of the logic subsystem 103 may be single or multi-core, and the programs executed thereon may be configured for parallel or distributed processing. The logic subsystem 103 may optionally include individual components that are distributed throughout two or more devices, which may be remotely located and/or configured for coordinated processing. One or more aspects of the logic subsystem 103 may be virtualized and executed by remotely accessible networked computing devices configured in a cloud computing configuration.

Data-holding subsystem 104 may include one or more physical, non-transitory devices configured to hold data and/or instructions executable by the logic subsystem 103 to implement the herein described methods and processes. When such methods and processes are implemented, the state of data-holding subsystem 104 may be transformed (for example, to hold different data).

Data-holding subsystem 104 may include removable media and/or built-in devices. Data-holding subsystem 104 may include optical memory (for example, CD, DVD, HD-DVD, Blu-Ray Disc, etc.), and/or magnetic memory devices (for example, hard drive disk, floppy disk drive, tape drive, MRAM, etc.), and the like. Data-holding subsystem 104 may include devices with one or more of the following characteristics: volatile, nonvolatile, dynamic, static, read/write, read-only, random access, sequential access, location addressable, file addressable, and content addressable. In some embodiments, logic subsystem 103 and data-holding subsystem 104 may be integrated into one or more common devices, such as an application-specific integrated circuit or a system on a chip.

It is to be appreciated that data-holding subsystem 104 includes one or more physical, non-transitory devices. In contrast, in some embodiments aspects of the instructions described herein may be propagated in a transitory fashion by a pure signal (for example, an electromagnetic signal) that is not held by a physical device for at least a finite duration. Furthermore, data and/or other forms of information pertaining to the present disclosure may be propagated by a pure signal.

When included, display subsystem 105 may be used to present a visual representation of data held by data-holding subsystem 104. As the herein described methods and processes change the data held by the data-holding subsystem 104, and thus transform the state of the data-holding subsystem 104, the state of display subsystem 105 may likewise be transformed to visually represent changes in the underlying data. Display subsystem 105 may include one or more display devices utilizing virtually any type of technology. Such display devices may be combined with logic subsystem 103 and/or data-holding subsystem 104 in a shared enclosure, or such display devices may be peripheral display devices.

When included, communication subsystem 106 may be configured to communicatively couple server 101 with one or more other computing devices, such as user device 121 and/or claims server 131. Communication subsystem 106 may include wired and/or wireless communication devices compatible with one or more different communication protocols. As non-limiting examples, communication subsystem 106 may be configured for communication via a wireless telephone network, a wireless local area network, a wired local area network, a wireless wide area network, a wired wide area network, etc. In some embodiments, communication subsystem 106 may allow server 101 to send and/or receive messages to and/or from other devices via a network such as the public Internet. For example, communication subsystem 106 may communicatively couple server 101 with user device 121 via network 113 and/or claims server 131 via network 117. In some examples, network 113 may be the public Internet. Furthermore, network 117 may be regarded as a private network connection and may include, for example, a virtual private network or an encryption or other security mechanism employed over the public Internet. In some examples, network 113 and network 117 may be the same network.

Further, the server 101 provides a network service that is accessible to a plurality of users through a plurality of client systems 121 communicatively coupled to the server 101 via a network 113. As such, computing environment 100 may include one or more devices operated by users, such as user device 121. User device 121 may be any computing device configured to access a network such as network 113, including but not limited to a personal computer, a laptop, a smartphone, a tablet, and the like. While two user devices or client systems 121 are shown, it should be appreciated that any number of user devices may be communicatively coupled to the server 101 via the network 113.

User device 121 includes a logic subsystem 123 and a data-holding subsystem 124. User device 121 may optionally include a display subsystem 125, communication subsystem 126, and/or other components not shown in FIG. 1. For example, user device 121 may also optionally include user input devices such as keyboards, mice, game controllers, cameras, microphones, and/or touch screens.

Logic subsystem 123 may include one or more physical devices configured to execute one or more instructions. For example, logic subsystem 123 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 123 may include one or more processors that are configured to execute software instructions. Additionally or alternatively, the logic subsystem 123 may include one or more hardware or firmware logic machines configured to execute hardware or firmware instructions. Processors of the logic subsystem 123 may be single or multi-core, and the programs executed thereon may be configured for parallel or distributed processing. The logic subsystem 123 may optionally include individual components that are distributed throughout two or more devices, which may be remotely located and/or configured for coordinated processing. One or more aspects of the logic subsystem 123 may be virtualized and executed by remotely accessible networking computing devices configured in a cloud computing configuration.

Data-holding subsystem 124 may include one or more physical, non-transitory devices configured to hold data and/or instructions executable by the logic subsystem 123 to implement the herein described methods and processes. When such methods and processes are implemented, the state of data-holding subsystem 124 may be transformed (for example, to hold different data).

Data-holding subsystem 124 may include removable media and/or built-in devices. Data-holding subsystem 124 may include optical memory (for example, CD, DVD, HD-DVD, Blu-Ray Disc, etc.), and/or magnetic memory devices (for example, hard drive disk, floppy disk drive, tape drive, MRAM, etc.), and the like. Data-holding subsystem 124 may include devices with one or more of the following characteristics: volatile, nonvolatile, dynamic, static, read/write, read-only, random access, sequential access, location addressable, file addressable, and content addressable. In some embodiments, logic subsystem 123 and data-holding subsystem 124 may be integrated into one or more common devices, such as an application-specific integrated circuit or a system on a chip.

When included, display subsystem 125 may be used to present a visual representation of data held by data-holding subsystem 124. As the herein described methods and processes change the data held by the data-holding subsystem 124, and thus transform the state of the data-holding subsystem 124, the state of display subsystem 125 may likewise be transformed to visually represent changes in the underlying data. Display subsystem 125 may include one or more display devices utilizing virtually any type of technology. Such display devices may be combined with logic subsystem 123 and/or data-holding subsystem 124 in a shared enclosure, or such display devices may be peripheral display devices.

When included, communication subsystem 126 may be configured to communicatively couple user device 121 with one or more other computing devices, such as server 101. Communication subsystem 126 may include wired and/or wireless communication devices compatible with one or more different communication protocols. As non-limiting examples, communication subsystem 126 may be configured for communication via a wireless telephone network, a wireless local area network, a wired local area network, a wireless wide area network, a wired wide area network, etc. In some embodiments, communication subsystem 126 may allow user device 101 to send and/or receive messages to and/or from other devices, such as server 101, via a network 113 such as the public Internet.

Similarly, claims server 131 may comprise a computing device communicatively coupled to server 101 via network 117. In some examples, claims server 131 may include one or more claims databases 133 that contain raw claims data, where the raw claims data may include information regarding health care treatments, services, costs, and so on.

Thus server 101, user devices 121, and claims server 131 may each represent computing devices which may generally include any device that is configured to perform computation and that is capable of sending and receiving data communications by way of one or more wired and/or wireless communication interfaces. Such devices may be configured to communicate using any of a variety of network protocols. For example, user device 121 may be configured to execute a browser application that employs HTTP to request information from server 101 and then displays the retrieved information to a user on a display.

Example interfaces that may be delivered to user device 121 from server 101 in such a manner and displayed, for example, on display subsystem 125 are described further herein and with regard to FIGS. 7-10.

Server 101 may collect and process data from claims server 131. Server 101 may analyze the collected data using, for example, data analysis techniques and/or artificial intelligence techniques. For example, claims data collected from claims server 131 may be analyzed to determine costs for a particular medical procedure. Analysis of claims data may further provide an overview of services and costs associated with particular health conditions and treatments for similar users. Server 101 may include one or more databases 111 in data-holding subsystem 104 for storing processed claims data. Systems and methods for determining treatment costs and timeframes are described further herein with regard to FIGS. 2-6.

Figure 2:
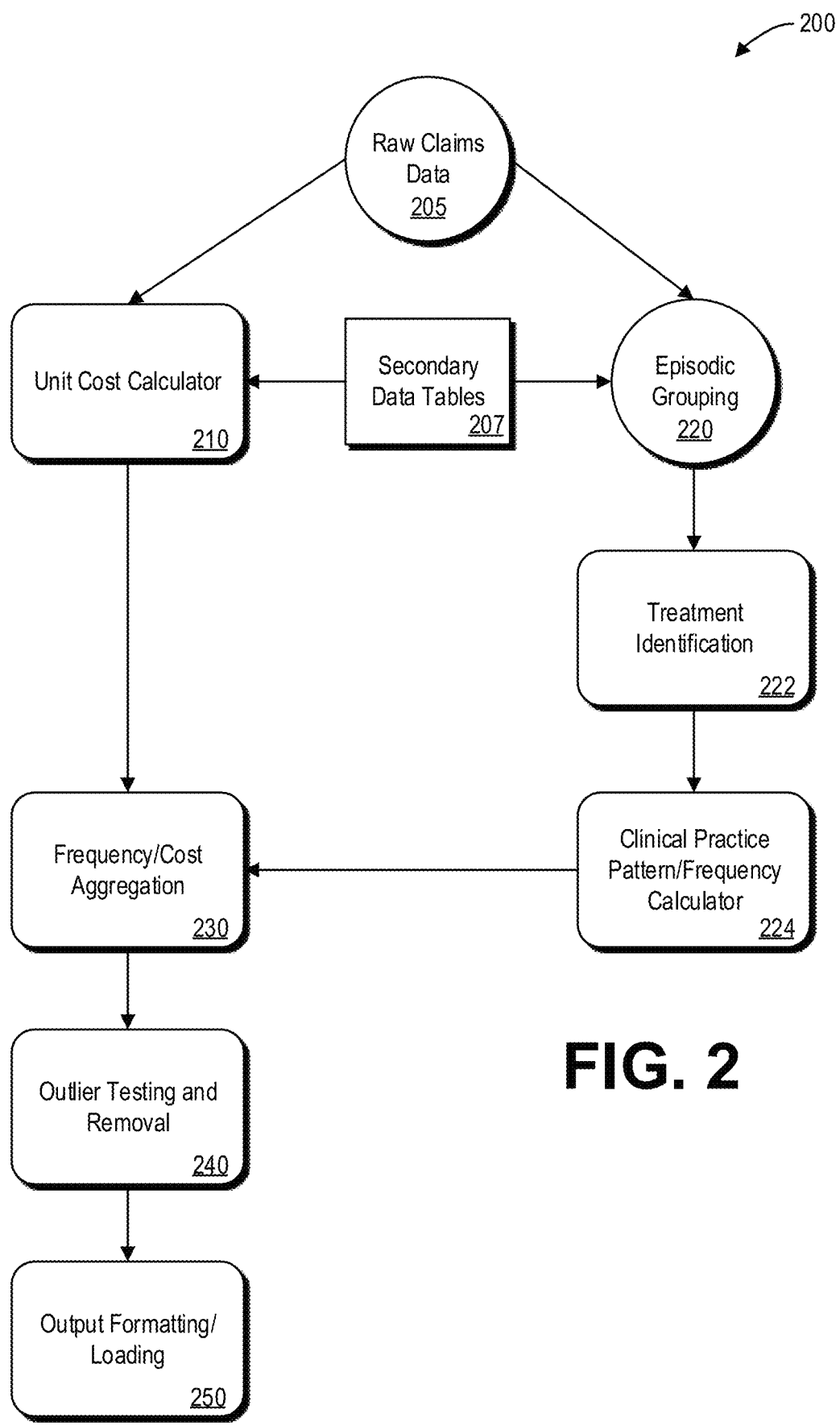
FIG. 2 shows an overview of an exemplary arrangement of software modules for implementing the functionality of a health care treatment cost estimator.

FIG. 2 shows an overview of an exemplary arrangement of software modules 200 for implementing the functionality of a health care treatment cost estimator. In particular, software modules 200 may include a raw claims data module 205, secondary data tables module 207, unit cost calculator module 210, episodic grouping module 220, treatment identification module 222, clinical practice pattern/frequency calculator module 224, frequency/cost aggregation module 230, outlier testing and removal module 240, and output formatting/loading module 250. Software modules 200 may, for example, be included as functional software in server 101.

Raw claims data module 205 may provide preprocessed claims data for data analysis. Raw claims data stored, for example, in claims server 131 may comprise upwards of hundreds of millions of claim lines that occupy hundreds of gigabytes in memory. However, data may be loaded into a volatile memory such as RAM for processing, and such large amounts of data may thus be impossible to read into memory due to memory constraints. Furthermore, given the massive amount of data, manual implementations using pen and paper are technically unfeasible for processing the raw claims data and calculating health care service and treatment statistics according to the processes and methods described herein. Raw claims data module 205 provides a technical solution to this technical problem. In particular, raw claims data module 205 facilitates data processing by using bash shell scripts to pre-filter the claims data and remove unneeded columns from the data. Raw claims data module 205 may partition the raw claims data into separate data sets based, for example, on client customer type (i.e., PPO, HMO, Medicare, etc.). Raw claims data module 205 may further partition the separated data sets by a member and date-of-service (member-DOS) key, where a member-DOS key identifies all claims relating to a single member on a particular DOS, for subsequent unit cost calculations. In this way, raw claims data may be broken down into a plurality of smaller data sets so that server 101 may load the smaller data sets into memory for processing.

Secondary data tables module 207 may provide, as non-limiting examples, secondary data tables that include detailed information relating to various health care classifications and codes. For example, secondary data tables module 207 may include a data table comprising plain-language descriptions for common procedure terminology (CPT) codes, International Classification of Diseases (ICD) codes, diagnosis-related groups (DRGs), episode treatment groups (ETGs), medical episode groupers (MEGs), and so on. Secondary tables module 207 may further include one or more fee schedule tables comprising established fees for medical procedures.

Unit cost calculator module 210 may use partitioned raw claims data to calculate statistics regarding health care service costs. In particular, unit costs for health care services are calculated on ungrouped claims data at the service level for professionals and facilities. In some examples, unit costs data outliers are addressed (e.g., removed from the data set) to prevent skewing. Health care claims often leave out important claim identifier fields such as CPT and diagnosis codes, and this is particularly true of outpatient facility claims. Current systems are unable to calculate the full cost of a health care treatment when facility claims do not include procedure codes tying the facility claim to a professional claim. Such claims must be attributed to a clinical service in order to represent the true cost of care to users. To resolve the technical problem, unit cost calculator module 210 may attribute facility claims to professional claims by weighting to the professional surgical charging occurring for the same member and date-of-service as the facility claims. Furthermore, in order to provide an accurate estimate of health care service costs, unit cost calculator module 210 may use the most recent year of ungrouped claims data to calculate unit costs. A method for a unit cost calculator module 210 is described further herein and with regard to FIG. 3.

Episodic grouping module 220 may further partition the separated data sets by one or more episode groupings, including but not limited to ETGs, MEGs, and so on, for subsequent treatment identification and service frequency calculations. While ETGs may be referred to herein, the use of ETGs as an episode grouping is exemplary only and is not intended to be limiting.

Treatment identification module 222 identifies treatment options within a particular ETG. Treatment identification module 222 utilizes built-in clinical expertise to identify treatments for each patient and claims associated with the treatment by using CPT, POS, provider specialty and ICD9 codes, DRGs, grouped information and additional fields. ETGs identify episodes with the same condition, but do not identify the specific surgery type used to treat the condition. In order to display the valid treatment options, treatment identification module 222 identifies the most common surgical paths within each ETG using CPT and diagnosis codes. This is accomplished through analysis of claims data to identify the proper combination of ETG, CPT, diagnosis, and POS. In some examples, medical professionals may review each surgical path identified for verification. A method for treatment identification module 222 is described further herein and with regard to FIG. 4.

Clinical practice pattern/frequency calculator module 224 calculates the frequency of services and stages of care within a treatment so that a user may know the probability that they will receive a particular service. Pattern/frequency calculator module 224 may apply a filter to treatments and services such that treatments and services with an occurrence probability less than a threshold, for example 5%, are removed. A method for clinical practice pattern/frequency calculator module 224 is described further herein and with regard to FIG. 5.

While health care service costs may vary over time, clinical practice patterns tend to not vary over time. In order to provide a larger data set for clinical practice pattern/frequency calculations, treatment identification module 222 and clinical practice pattern/frequency calculator module 224 may utilize the most recent two years of claims data.

Frequency/cost aggregation module 230 joins unit cost calculations and clinical practice pattern/frequency calculations. In particular, frequency/cost aggregation module 230 connects the unit costs calculated by unit cost calculator module 210 to each service frequency calculated by pattern/frequency calculator module 224. A method for frequency/cost aggregation 230 is described further herein and with regard to FIG. 6.

In some examples, cost and frequency estimates are aggregated at a regional level. Regional cost estimates may be provided at the smallest geographical granularity possible without limiting the number of estimates. In some examples, zip code level aggregations of data may be utilized as the smallest geographical granularity. If the resulting claim volume is insufficient to provide statistically accurate estimates, for example less than thirty services, then statewide averages may be used. If there is not enough data at a state level, regional averages including neighboring states may be used.

Outlier testing and removal module 240. While various outlier and quality assurance tests are performed by each module during processing, outlier testing and removal module 240 performs additional outlier testing to ensure all data is consistent with reference points and all expected components of a treatment are present.

Output formatting/loading module 250 generates user-friendly interfaces to display the aggregated, processed data. For example, output formatting/loading module 250 may generate interfaces that display health care treatment options, services, and savings opportunities for different health conditions. Such interfaces may display to users when savings opportunities exist within each service type. Example interfaces are described further herein and with regard to FIGS. 7-10.

Figure 3:
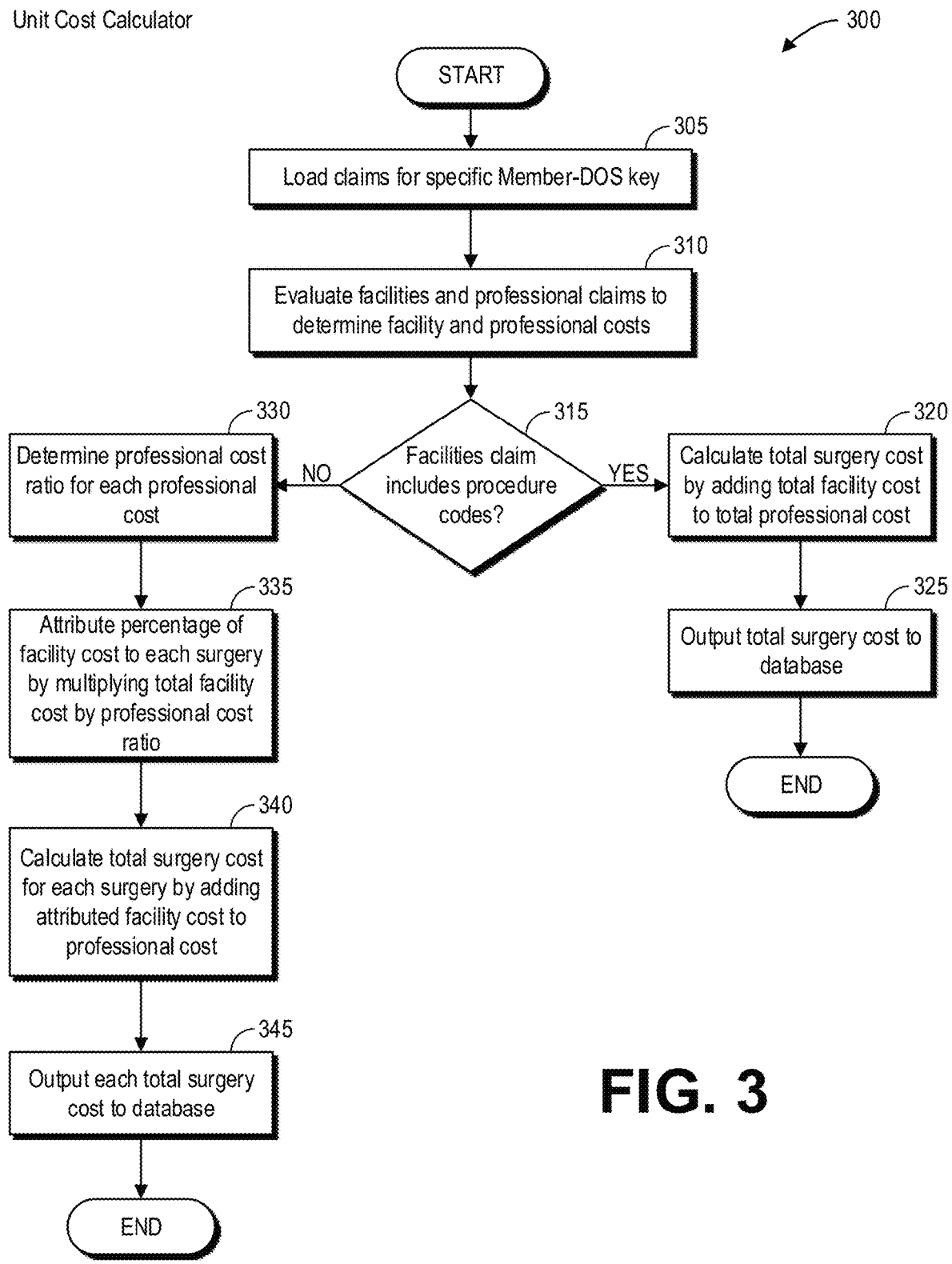
FIG. 3 shows a high-level flow chart illustrating an example method for calculating unit cost of health care services.

FIG. 3 shows a high-level flow chart illustrating an example method 300 for calculating unit cost of health care services. In particular, method 300 relates to attributing facilities costs to professional costs in order to provide an accurate cost estimate for a given health care service. Claims data is not partitioned by ETG, so that unit costs are calculated for services regardless of the related overall treatment. Method 300 may be stored as executable instructions in non-transitory memory on server 101.

Method 300 may begin at 305. At 305, method 300 may include loading claims for a specific Member-DOS key. Loading claims may comprise reading a data set into memory for processing. The Member-DOS key identifies all claims relating to a specific member, or patient, for a particular DOS.

At 310, method 300 may include evaluating facilities and professional claims to determine facility and professional costs. At 315, method 300 may include determining if the facilities claim includes procedure codes.

If the facilities claim includes procedure codes, method 300 may proceed to 320. Since the facilities claim includes procedure codes, the facility cost may be accurately correlated to a professional cost. Thus, at 320, method 300 may include calculating the total surgery cost by adding the total facility cost to the total professional cost. At 325, method 300 may include outputting the total surgery cost to a database 111. Method 300 may then end.

Returning to 315, if the facilities claim does not include procedure codes, method 300 may proceed to 330. At 330, method 300 may include determining a professional cost ratio for each professional cost. For example, if a patient receives two surgeries on one day, there may be a professional claim for each surgery. The first professional claim may include a cost for the first surgery and the second professional claim may include a cost for the second surgery. The total professional cost is the sum of the first cost and the second cost. A professional cost ratio is the percentage of one professional cost out of the total professional cost.

At 335, method 300 may include attributing a percentage of the facility cost to each surgery by multiplying the total facility cost by the professional cost ratio. At 340, method 300 may include calculating the total surgery cost for each surgery by adding the attributed facility cost to the professional cost. At 345, method 300 may include outputting each total surgery cost to the database. Method 300 may then end.

As a non-limiting illustrative example, consider a patient who receives two surgeries in one day at the same hospital. The first surgery may cost $2,000 while the second surgery may cost $1,000. Then the professional cost ratio of the first surgery is 67% while the professional cost ratio of the second surgery is 33%. The facility costs may be, in total, $16,000. Then the facility cost attributed to the first surgery may be $10,667 (67% of $16,000) while the facility cost attributed to the second surgery may be $5,333 (33% of $16,000). The total cost of the first surgery including the attributed facility cost may be $12,667 while the total cost of the second surgery including the attributed facility cost may be $6,333.

Method 300 may be applied to each member-DOS key in the full claims data set. After a total cost for each service including professional costs and facility costs is calculated using method 300, unit cost calculator 210 may calculate the average cost of each health care service. In some examples, unit cost calculator 210 may use the most recent year of claims data to calculate the average cost of each health care service.

In some examples, the method may weight more recent claims data heavier than older claims data to provide additional accuracy in the unit cost calculation. Further, in some examples the method may further include updating the unit cost calculations by utilizing a multiplier. For example, if it is known that a fee schedule will soon be updated such that the unit cost calculations based on historical claims will be outdated, the method may update the unit cost calculations with a multiplier (e.g., the multiplier may scale the unit cost calculations based on the difference between a previous fee schedule and an updated fee schedule).

Figure 4:
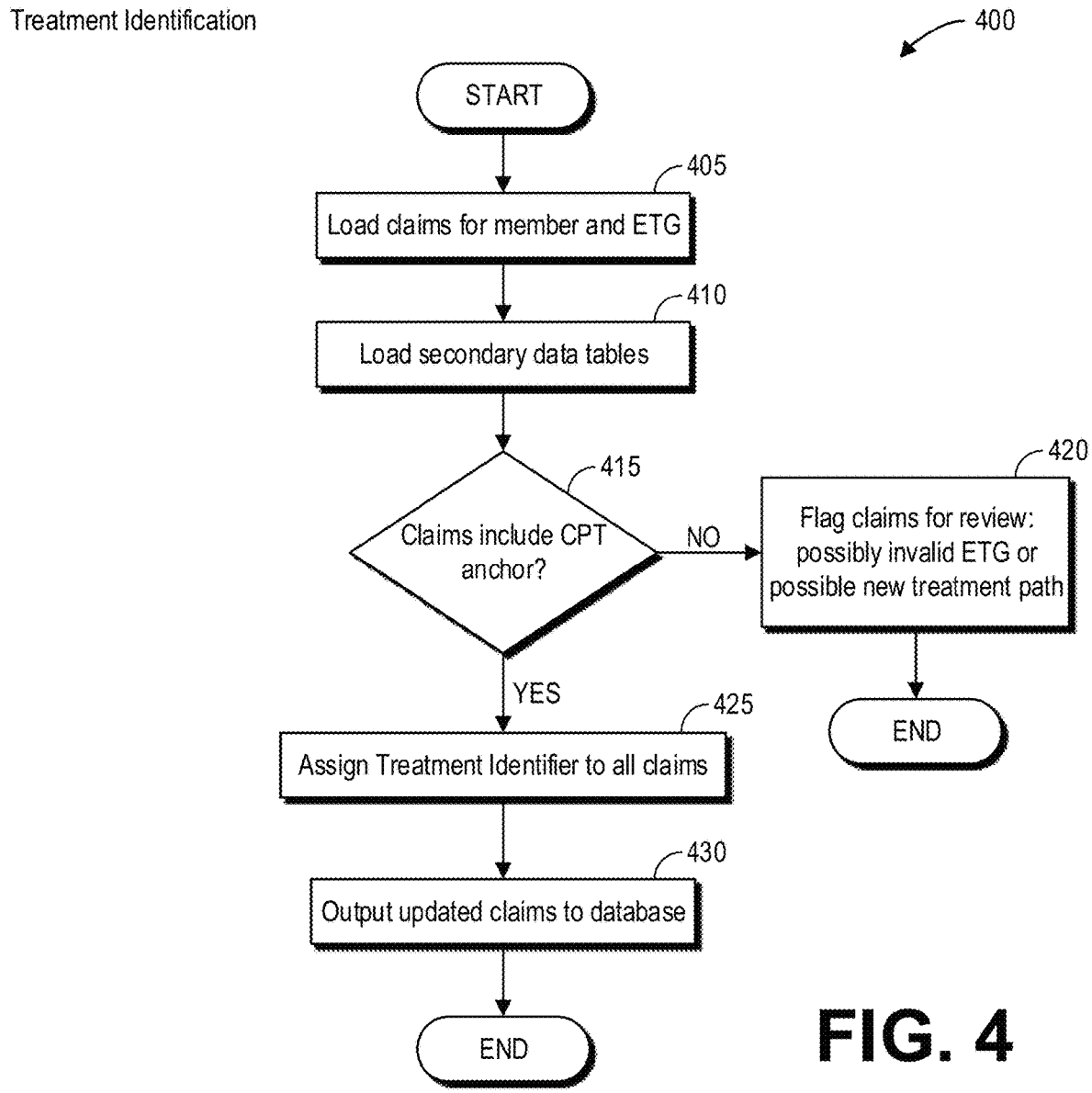
FIG. 4 shows a high-level flow chart illustrating an example method for identifying treatments within an episodic grouping.

FIG. 4 shows a high-level flow chart illustrating an example method 400 for identifying treatments within an episodic grouping. In particular, method 400 may provide the functionality for treatment identification module 222. Method 400 may be stored as executable instructions in non-transitory memory on server 101.

Method 400 may begin at 405. At 405, method 400 may include loading claims for a member and an episode grouping (e.g., ETG or MEG). Loading claims may comprise, for example, reading claims data into local memory in server 101 for processing. At 410, method 400 may include loading secondary data tables. Secondary data tables may include, for example, a set of CPT anchors related to the ETG. A CPT anchor may comprise a CPT code that identifies a specific surgical path within an ETG.

At 415, method 400 may include determining if the claims include a CPT anchor. If the claims do not include a CPT anchor, method 400 may proceed to 420. At 420, method 400 may include flagging the claims for review. In some examples, the absence of a CPT anchor indicates that the ETG listed in the claims is incorrect or invalid. In other examples, the absence of a CPT anchor indicates a possible new treatment path that was not pre-specified. Method 400 may then end.

Returning to 415, if the claims include a CPT anchor, method 400 may proceed to 425. At 425, method 400 may include assigning a treatment identifier to all claims based on the CPT anchor. The treatment identifier may comprise a key code that identifies the claims as belonging to a specific treatment within an ETG.

At 430, method 400 may include outputting the updated claims to a database. Outputting the claims updated with a treatment identifier may comprise writing the claims to a database, such as database 111. Method 400 may then end.

Figure 5:
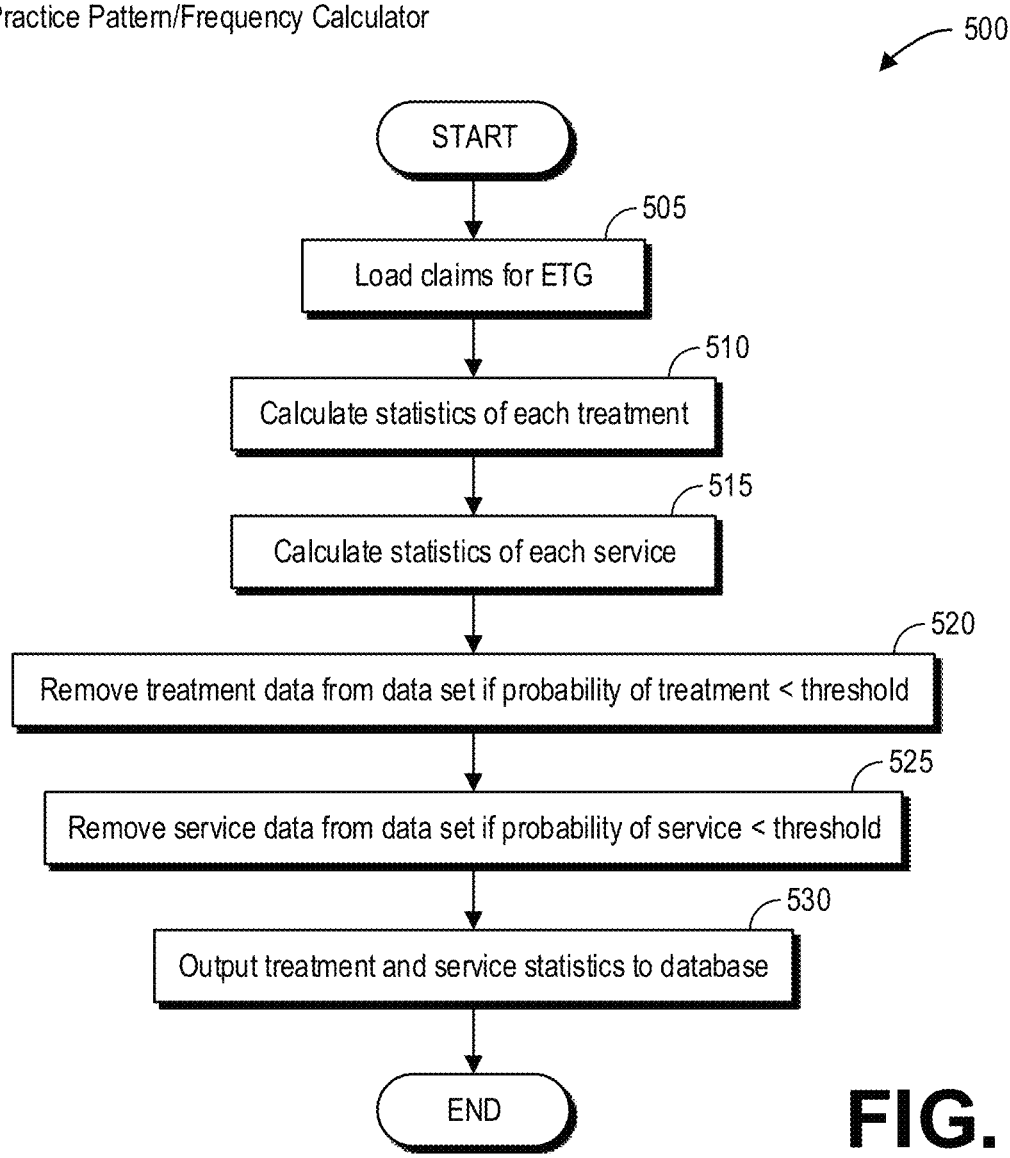
FIG. 5 shows a high-level flow chart illustrating an example method for calculating clinical practice patterns and frequencies for a health care treatment.

FIG. 5 shows a high-level flow chart illustrating an example method 500 for calculating clinical practice patterns and frequencies for a health care treatment. Method 500 may be stored as executable instructions in non-transitory memory on server 101.

Method 500 may begin at 505. At 505, method 500 may include loading claims for a given ETG. Loading claims for an ETG may comprise reading claims data for an ETG into local memory in server 101 to facilitate processing the claims data. The claims for a given ETG may include the treatment identifier added to the data by method 400.

At 510, method 500 may include calculating statistics of each treatment. Calculating statistics of each treatment may comprise, for example, calculating the frequency for each treatment within the given ETG. In this way, a user may know how many people choose a particular treatment for a health condition.

At 515, method 500 may include calculating statistics of each service. Calculating statistics of each service may include, for example, calculating the frequency of each service within a particular treatment. Calculating statistics of a service may include calculating the average time after the beginning of the treatment that the service occurs. If a service is the CPT anchor for the treatment, then the service may be the primary service for the treatment. If a service is not the CPT anchor for the treatment, then the service may be labelled as belonging in an "Evaluation" phase if the service occurs before the primary service or in a "Follow-up" phase if the service occurs after the primary service.

At 520, method 500 may include removing treatment data from the data set if the frequency of the treatment is less than a threshold. In some examples, the threshold may be 5%. In other examples, the threshold may be greater than or less than 5%. The threshold may be chosen such that if the frequency of the treatment is less than the threshold, the treatment is relatively uncommon and may only be pursued in response to a physician's recommendation.

At 525, method 500 may include removing service data from the data set if the frequency of the service is less than a threshold. In some examples, the threshold may be 5%. In other examples, the threshold may be greater than or less than 5%. The threshold may be chosen such that if the frequency of the service is less than the threshold, the service is relatively uncommon and may only be pursued upon a physician's recommendation. Filtering the data in this way eliminates outliers that may skew the data and/or unnecessarily increase the complexity of options displayed to a user.

At 530, method 500 may include outputting treatment and service statistics to a database. Outputting treatment and service statistics to a database may comprise writing the statistics to a table in the database. Method 500 may then end.

Figure 6:
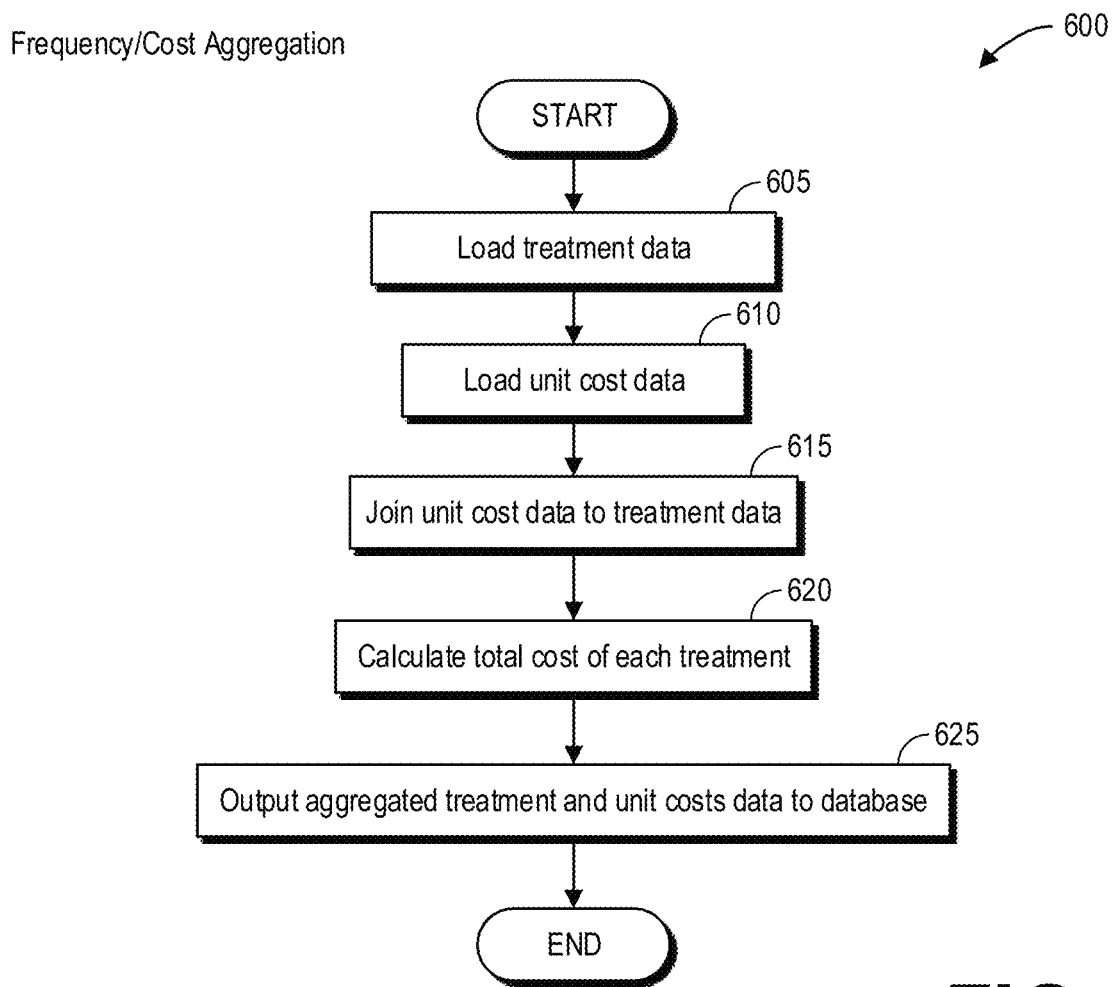
FIG. 6 shows a high-level flow chart illustrating an example method for aggregating calculated frequencies and costs of health care treatments.

FIG. 6 shows a high-level flow chart illustrating an example method 600 for aggregating calculated frequencies and costs of health care treatments. Method 600 may be stored as executable instructions in non-transitory memory on server 101.

Method 600 may begin at 605. At 605, method 600 may include loading treatment data. Loading treatment data may include reading into memory the treatment and service statistics data processed by treatment identification module 222 and clinical practice pattern/frequency calculator module 224.

At 610, method 600 may include loading unit cost data. Loading unit cost data may comprise reading into memory the unit cost data calculated by the unit cost calculator module 210.

At 615, method 600 may include joining the unit cost data to the treatment data. Joining the unit cost data to the treatment data may comprise assigning the average cost of a service to each service in the treatment data.

At 620, method 600 may include calculating the total cost of each treatment. Calculating the total cost of each treatment may comprise summing the cost of each service within a treatment.

At 620, method 600 may include outputting the aggregated treatment and unit costs data to a database. Method 600 may then end.

In some examples, after server 101 processes and aggregates health care treatment data as described hereinabove, a user of user device 121 may access the data via user-friendly interfaces, such as the interfaces shown in FIGS. 7-10. In such examples, server 101 may also function as a web server providing a network service that is accessible to a plurality of users of a plurality of client systems communicatively coupled to server 101 via a network. The network service is operable to receive, from a user of one of the client systems, an indication of a selected medical condition and/or treatment. The network service is further operable to transmit statistics regarding the selected medical condition and/or treatment to the user via the client system. These statistics may be rendered in a user interface implemented at the client system. In this way, the calculations obtained using the systems and methods depicted and described herein with regard to FIGS. 2-6 may be particularly formatted and displayed to a user via, as non-limiting examples, the interfaces shown in FIGS. 7-10.

Figure 7:
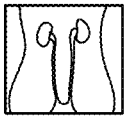
FIG. 7 illustrates an example interface providing an overview of available treatments for a specified condition.

FIG. 7 illustrates an example interface 700 providing an overview of available treatments for a specified medical condition. In particular, interface 700 displays three identified treatments for kidney stones and the estimated total cost of each treatment. While the example depicted in FIG. 7 shows treatments for kidney stones, in other examples treatments for a different medical condition may be displayed.

Interface 700 includes a search tool 705 and a browse tool 710 that enables a user to search for treatment options 715 and estimated costs 718 for any medical condition 720. Interface 700 may further display a location or search area 725 of the user which may be utilized to display regional cost estimates. A user of interface 700 may select one of the treatment options to view more detailed information about the selected treatment option. As shown in FIG. 7, treatment options may include both surgical operations and non-surgical treatments. In this way, a user can view a variety of treatment options and consider the total costs when selecting a treatment option.

Figure 8:
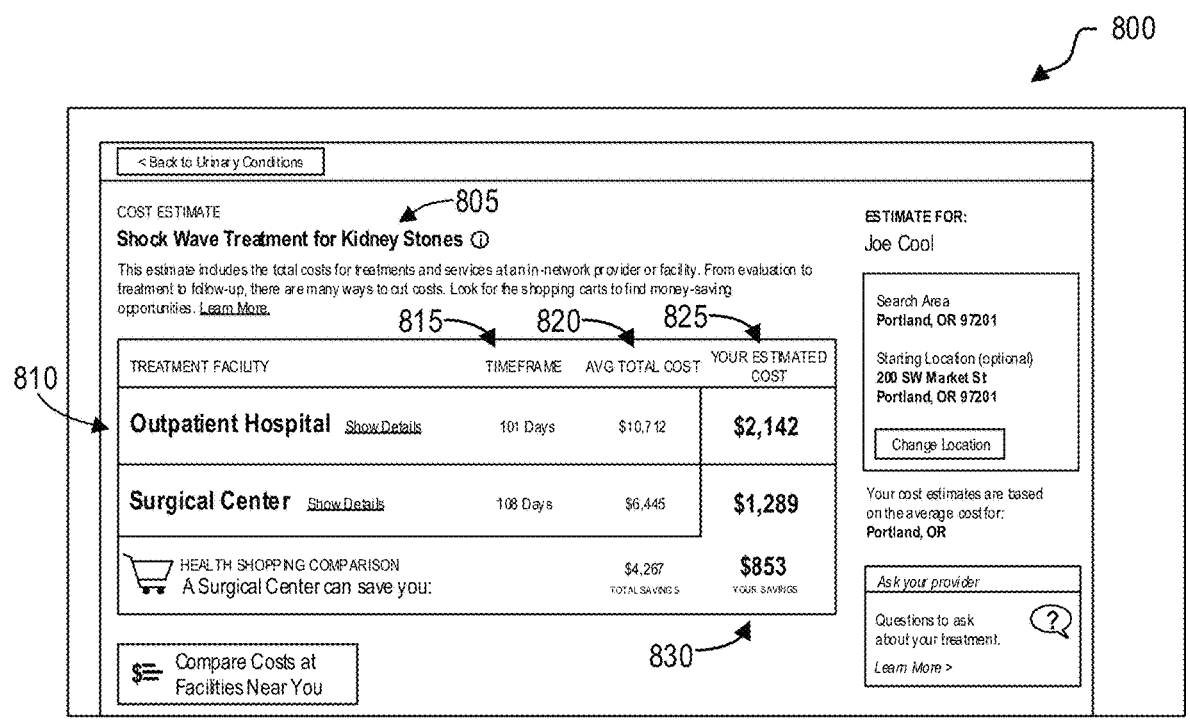
FIG. 8 illustrates an example interface providing an overview of place-of-service options for a specified treatment.

FIG. 8 illustrates an example interface 800 providing an overview of place-of-service options for a specified treatment. Once a treatment option 805 is selected by a user, the appropriate places of service 810 are identified. In particular, interface 800 displays the various treatment facilities 810 for a shock wave treatment for kidney stones. For each facility, interface 800 displays an estimated timeframe 815 of the treatment at the facility and the average total cost 820 of the treatment at the facility. In some examples, interface 800 may further display an estimated total cost 825 for the user based on a health insurance plan for the user. In such examples, the estimated total cost for the user may take into account any deductibles, coinsurance, copayments, and so on.

Interface 800 may also display a highlighted comparison 830 of the facility options, where the comparison may emphasize the difference in overall total cost and total cost for the user. In this way, a user may easily identify place-of-service savings for health care treatments. For example, as shown in FIG. 8, the average total cost of receiving shock wave treatment for kidney stones at an outpatient hospital may be $10,712, while the average total cost for the same treatment at a surgical center may be $6,445. Interface 800 may indicate that the treatment at the surgical center costs $4,267 less than the same treatment at the outpatient hospital.

Figure 9:
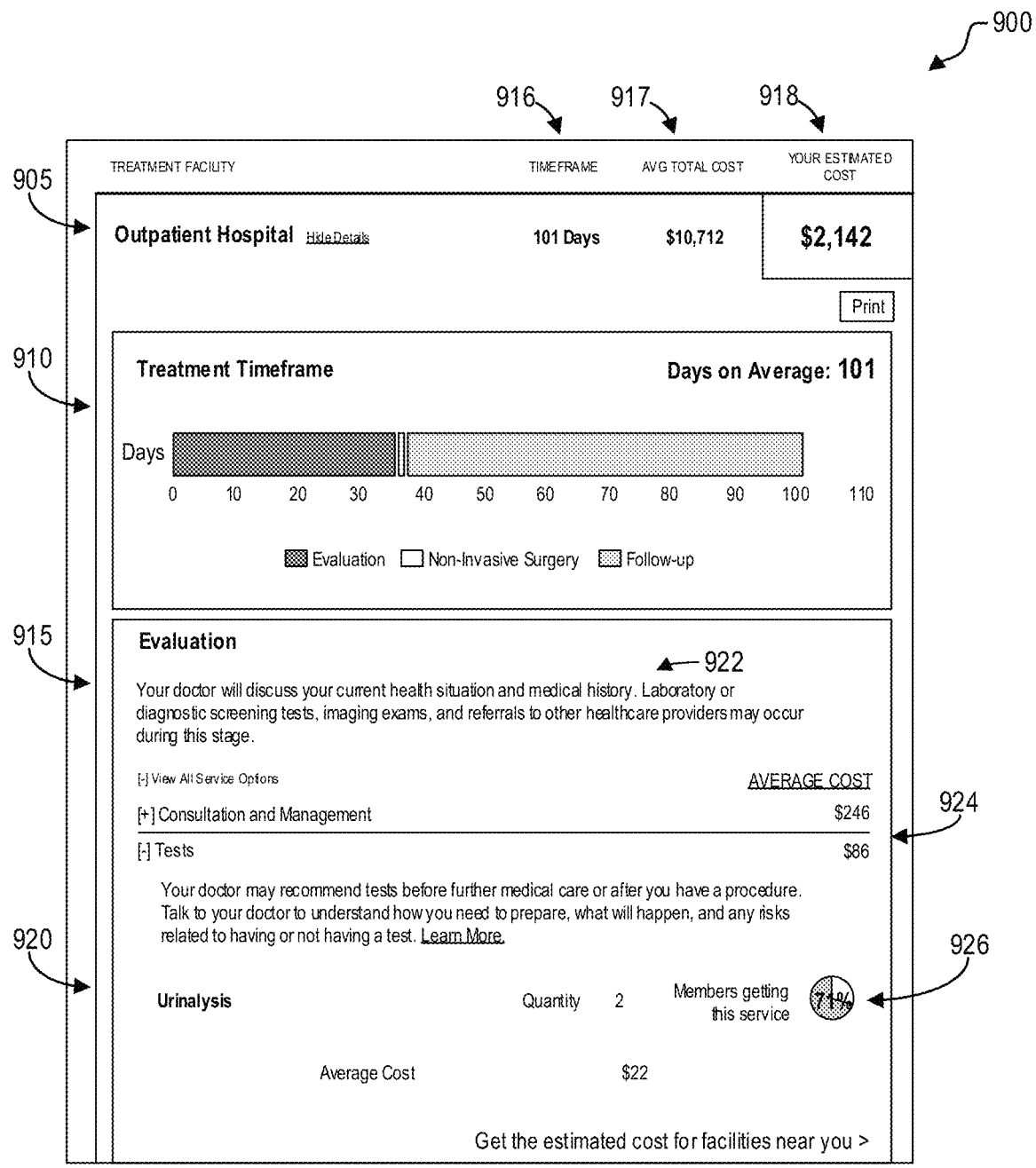
FIG. 9 illustrates an example interface providing an overview of a treatment at a specified place-of-service.

FIG. 9 illustrates an example interface 900 providing an overview of a treatment at a specified place-of-service 905. In particular, interface 900 shows a treatment timeline 910, stages of care 915, and service-level details for a selected treatment option. In the example depicted, the outpatient hospital is the selected place-of-service or facility 905. Interface 900 may display the estimated timeframe 916, the average total cost 917, and the estimated total cost to the user 918 based on the user's health insurance. Interface 900 may include a treatment timeline 910 that visually outlines the treatment according to treatment phases. For example, a health care treatment may comprise three treatment stages: evaluation, non-invasive surgery, and follow-up. The treatment timeline 910 may show the average time for each treatment stage. Below the treatment timeline 910, interface 900 may include detailed information regarding each treatment stage and the various health care services that comprise each treatment stage. For example, an evaluation stage may include a consultation with a physician and a urinalysis test. As shown in FIG. 9, interface 900 may include a description 922 of the evaluation stage, the average cost 924 of each health care service, and the percentage of patients 926 who receive each health care service. For example, interface 900 includes a pie chart 926 illustrating that 71% of members purchase the urinalysis service. In this way, a user may understand what to expect during a health care treatment of a specified medical condition, such as what services the user may purchase, the cost of each service, and the timeline. Understanding the treatment timeframe may be especially beneficial for the user, who may use the information to take out-of-pocket health care costs into considerations when budgeting. Furthermore, in some examples a user may choose to pursue a treatment option or a facility option that is more expensive overall, but where the costs of each service are relatively low and distributed over time.

Figure 10:
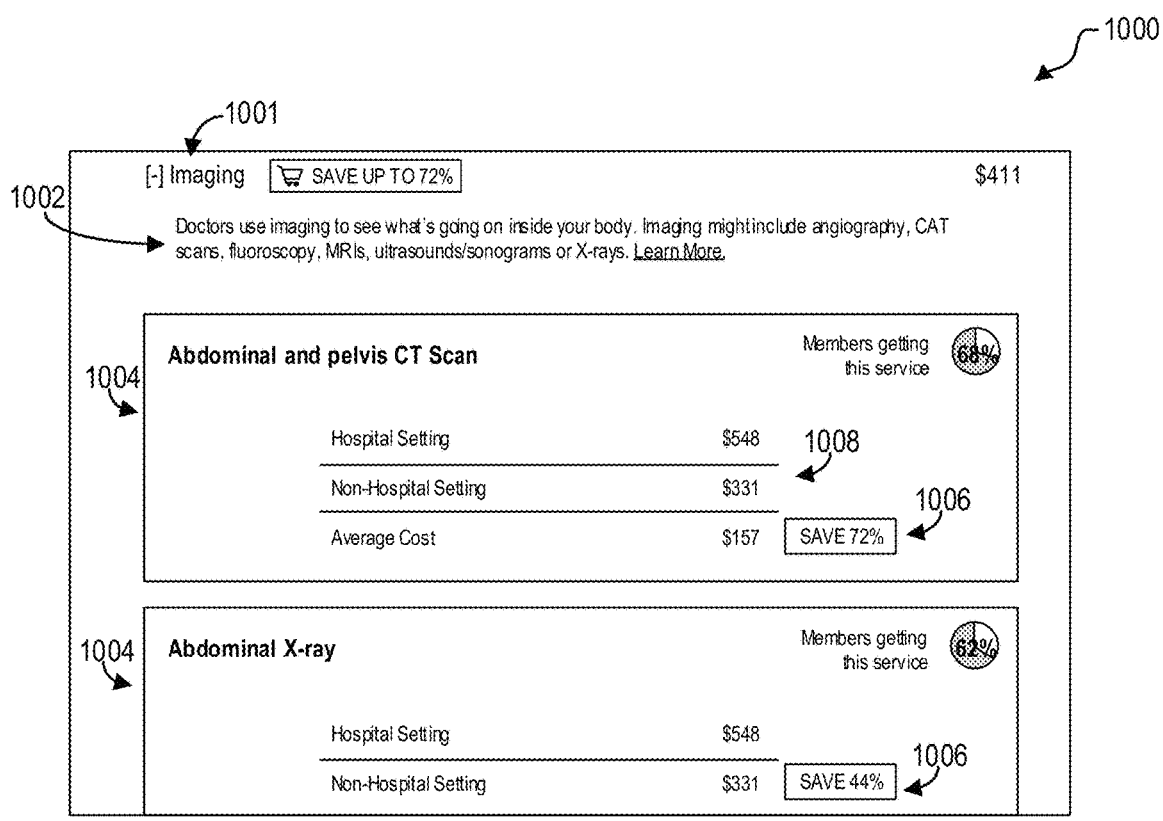
FIG. 10 illustrates an example interface providing an overview of place-of-service savings opportunities for a specific health care service.

FIG. 10 illustrates an example interface 1000 providing an overview of place-of-service savings opportunities for a specific health care service. Interface 1000 may be displayed to a user of interface 900, for example, when the treatment option includes imaging services 1001. Interface 1000 includes a summary description 1002 of imaging services, different options 1004 for imaging services, and place-of-service savings 1006 for each imaging service option. As shown, the cost of health care services may differ for hospital settings and non-hospital settings. Interface 1000 may display the average cost 1008 of the imaging service at each location. Interface 1000 may further include statistical information regarding each imaging service, such as the percentage of members who get the service during the treatment.

The present invention enables the breadth and depth of health care treatment statistics obtained using the methods shown in FIGS. 3-6 and displayed via the interfaces illustrated by FIGS. 7-10.

Thus, systems, apparatuses, and methods for calculating health care statistics are provided. In one embodiment, a system, comprises a data-holding subsystem configured to hold raw medical claims data in non-transitory memory, and a logic subsystem configured to partition the raw medical claims data into a plurality of data sets based on one or more of insurance type, episode grouping, member key, date-of-service key, or a combination thereof. The logic subsystem is further configured to calculate statistics based on each of the plurality of data sets and output correlated calculation results for display on a user device, wherein the statistics include a frequency of patients receiving a health care service and an average cost of the health care service.

In a first example of the system, the logic subsystem partitions the raw medical claims data into the plurality of data sets using bash shell scripts. In a second example of the system optionally including the first example, the logic subsystem is further configured to calculate the frequency of patients receiving the health care service from a first data set partitioned by the episode grouping. In a third example of the system optionally including one or more of the first and second examples, the logic subsystem is further configured to calculate the average cost of the health care service from a second data set partitioned by the member key and the date-of-service key. In a fourth example of the system optionally including one or more of the first through third examples, the average cost includes a facility cost and a professional cost, the facility cost is weighted to the health care service based on the professional cost. In a fifth example of the system optionally including one or more of the first through fourth examples, the first data set includes medical claims for a first period and the second data set includes medical claims data for a second period, the first period greater than the second period. In a sixth example of the system optionally including one or more of the first through fifth examples, the correlated calculation results comprise the frequency of patients receiving the health care service correlated to the average cost of the health care service.

In another embodiment, a computer-implemented method for processing raw medical claims comprises: partitioning the raw medical claims into a plurality of data sets based on patient key and date-of-service key; reading a data set of the plurality of data sets for a specified patient and date of service into non-transitory memory for processing, the data set including a professional claim and a facility claim; determining a professional cost ratio based on the professional claim; attributing at least a portion of the facility claim to the professional claim based on the professional cost ratio; and writing a sum of the at least the portion of the facility claim and the professional claim to a database in the non-transitory memory.

In a first example of the method, attributing at least the portion of the facility claim to the professional claim comprises multiplying the facility claim by the professional cost ratio. In a second example of the method optionally including the first example, the method further comprises transmitting the sum to a user device for display in a user interface.

In yet another embodiment, an apparatus comprises: a logic subsystem providing a network service that is accessible to a plurality of users through a plurality of client systems communicatively coupled to the server via a network; and a data-holding subsystem storing a medical claims database that is maintained by the logic subsystem, the medical claims database comprising a plurality of medical claims information records respectively associated with a plurality of medical claims, each medical claim information record comprising an indication of an insurance type, an indication of a episode grouping, an indication of a member key, and an indication of a date-of-service key; wherein the logic subsystem is configured to: partition the plurality of medical claims information records into a plurality of data sets based on one or more of the indication of the insurance type, the indication of the episode grouping, the indication of the member key, the indication of the date-of-service key, or a combination thereof; and calculate statistics based on each of the plurality of data sets, the statistics comprising a frequency of patients receiving a health care service and an average cost of the health care service; wherein, upon being accessed by a user of one of the client systems, the network service is operable to receive an indication from the client system of a selected health care treatment being selected from a plurality of health care treatments, and wherein, upon receiving the indication of the selected health care treatment, the network service is operable to transmit the statistics to the client system for rendering a user interface implemented at the client system, the user interface comprising: a timeline for the selected health care treatment, the timeline displaying an average duration for each of an evaluation phase, a treatment phase, and a follow-up phase; and an outline of health care services associated with the evaluation phase, the treatment phase, and the follow-up phase, the outline displaying the statistics for each of the health care services.

In a first example of the apparatus, the user interface further comprises an average total cost and an estimated out-of-pocket cost of the selected health care treatment. In a second example of the apparatus optionally including the first example, the average total cost and the estimated out-of-pocket cost of the selected health care treatment are calculated by the logic subsystem based at least in part on a type of health care facility providing the health care treatment. In a third example of the apparatus optionally including one or more of the first and second examples, the average total cost and the estimated out-of-pocket cost of the selected health care treatment are calculated by the logic subsystem by summing the cost of each health care service within the selected health care treatment. In a fourth example of the apparatus optionally including one or more of the first through third examples, the statistics further include a frequency of each health care treatment within an episode grouping, wherein each treatment comprises at least one health care service. In a fifth example of the apparatus optionally including one or more of the first through fourth examples, the statistics further include the frequency of patients receiving a health care service within a health care treatment. In a sixth example of the apparatus optionally including one or more of the first through fifth examples, the outline of the health care services does not include a health care service for which the frequency of patients receiving the health care service is below a threshold. In a seventh example of the apparatus optionally including one or more of the first through sixth examples, the threshold comprises 5%. In an eighth example of the apparatus optionally including one or more of the first through seventh examples, the statistics further include the average time that a health care service occurs after the beginning of a health care treatment. In a ninth example of the apparatus optionally including one or more of the first through eighth examples, the timeline is generated based on the statistics.

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application.

Such claims, whether broader, narrower, equal, or different in scope to the original claims, are also regarded as included within the subject matter of the present disclosure.

The invention claimed is:

1. A system, comprising:
a data-holding subsystem storing raw medical claims data in non-transitory memory, the raw medical claims data comprising a plurality of medical insurance claims in different non-standardized formats received from a plurality of health care providers for a plurality of health care services provided to a plurality of patients at a plurality of health care facilities, wherein a file size of the raw medical claims data exceeds a storage capacity of a volatile memory of the data-holding subsystem; and
a logic subsystem comprising a processor, the data-holding subsystem further storing executable instructions in the non-transitory memory that when executed by the logic subsystem cause the logic subsystem to:
convert the raw medical claims data into a plurality of data sets by pre-filtering the raw medical claims data, removing unneeded data from the raw medical claims data, and partitioning the raw medical claims data based on one or more of insurance type, episode grouping, member key, date-of-service key, or a combination thereof to obtain the plurality of data sets with a standardized format corresponding to the partitioning for each data set of the plurality of data sets, the plurality of data sets including a first data set partitioned by the member key and the date-of-service key, wherein a file size of each of the plurality of data sets is smaller than the storage capacity of the volatile memory;
store the plurality of data sets in the non-transitory memory of the data-holding subsystem;
load each of the plurality of data sets into the volatile memory;
calculate statistics based on each of the plurality of data sets while each of the plurality of data sets is loaded in the volatile memory, wherein calculating the statistics includes calculating an average cost of a health care service based on the first data set;
store the calculated statistics in a database in the non-volatile memory;
provide, to users of a plurality of user devices, remote access over a network so any of the users can update selections of health care services from a plurality of health care services indicated in a graphical user interface, the plurality of health care services determined from a data set of the plurality of data sets;
receive, from a user via a user device communicatively coupled to the logic subsystem via the network, an indication of the health care service selected by the user from the plurality of health care services displayed to the user in the graphical user interface via the user device;
automatically correlate and format, responsive to receiving the indication of the selected health care service from the user device, calculation results for the selected health care service from the calculated statistics; and
transmit, via the network to the user device for display to the user in the graphical user interface, the correlated and formatted calculation results, wherein the calculated statistics of the correlated and formatted calculation results include a frequency of patients receiving the health care service and the average cost of the health care service, wherein the user device displays the graphical user interface depicting the correlated and formatted calculation results to the user upon receiving the transmission of the correlated and formatted calculation results.

2. The system of claim 1, wherein the logic subsystem partitions the raw medical claims data into the plurality of data sets using bash shell scripts.

3. The system of claim 1, wherein the logic subsystem is further configured to calculate the frequency of patients receiving the health care service from a second data set of the plurality of data sets partitioned by the episode grouping.

4. The system of claim 3, wherein the average cost of the health care service includes a facility cost and a professional cost, the facility cost weighted to the health care service based on the professional cost.

5. The system of claim 3, wherein the first data set includes medical claims data for a first period and the second data set includes medical claims data for a second period, the first period less than the second period.

6. The system of claim 5, wherein the correlated and formatted calculation results comprise the frequency of patients receiving the health care service correlated to the average cost of the health care service.

7. A computer-implemented method for processing raw medical claims, comprising:
automatically converting, with a processor, the raw medical claims in a first format into a plurality of data sets in a second format by partitioning the raw medical claims based on a patient key and a date-of-service key, wherein a file size of the raw medical claims exceeds a storage capacity of a volatile memory communicatively coupled to the processor and wherein a file size of each of the plurality of data sets is smaller than the storage capacity of the volatile memory, the second format corresponding to the partitioning of the raw medical claims;
storing the plurality of data sets in non-transitory memory;
reading, with the processor, a data set of the plurality of data sets for a specified patient and date of service into the volatile memory for processing, the data set including a professional claim and a facility claim;
automatically determining, with the processor, a professional cost ratio based on the professional claim;
automatically attributing, with the processor, at least a portion of the facility claim to the professional claim based on the professional cost ratio;
automatically writing, with the processor, a sum of the at least the portion of the facility claim and the professional claim to a database in the non-transitory memory communicatively coupled to the processor;
providing, with the processor over a network, remote access to a plurality of user devices;
receiving, with the processor from a user device over the network, an indication of a health care service selected by a user of the user device;
automatically determining, with the processor from sums corresponding to the health care service retrieved by the processor from the database, a first average cost for the health care service at a first facility and a second average cost for the health care service at a second facility; and
transmitting, with the processor over the network to the user device for display to the user, a graphical user interface depicting the first average cost for the health care service at the first facility and the second average cost for the health care service at the second facility.

8. The computer-implemented method of claim 7, wherein attributing at least the portion of the facility claim to the professional claim comprises multiplying the facility claim by the professional cost ratio.

9. The computer-implemented method of claim 7, further comprising determining a first estimated cost and a second estimated cost for the user based on the first average cost and the second average cost, respectively, according to a health insurance plan for the user, wherein the graphical user interface further depicts the first estimated cost and the second estimated cost.

10. An apparatus, comprising:
a logic subsystem providing a network service that is remotely accessible to a plurality of users through a plurality of client systems communicatively coupled to a server via a network; and
a data-holding subsystem storing a medical claims database that is maintained by the logic subsystem, the medical claims database comprising a plurality of medical claims information records respectively associated with a plurality of medical claims, each medical claim information record comprising an indication of an insurance type, an indication of an episode grouping, an indication of a member key, and an indication of a date-of-service key in a first format;
wherein the logic subsystem, upon executing instructions stored in non-transitory memory of the data-holding subsystem, is configured to:
automatically convert the plurality of medical claims information records in the first format into a plurality of data sets in a second format by partitioning the plurality of medical claims information records based on one or more of the indication of the insurance type, the indication of the episode grouping, the indication of the member key, the indication of the date-of-service key, or a combination thereof, wherein a file size of the plurality of medical claims information records exceeds a storage capacity of a volatile memory of the data-holding subsystem, and wherein a file size of each of the plurality of data sets is smaller than the storage capacity of the volatile memory;
store the plurality of data sets in the non-transitory memory;
load each of the plurality of data sets into the volatile memory; and
automatically calculate statistics based on each of the plurality of data sets while each of the plurality of data sets is loaded in the volatile memory, the statistics comprising a frequency of patients receiving a health care service and an average cost of the health care service;
wherein, upon being remotely accessed by a user of one of the client systems, the network service is operable to receive an indication from the client system of a selected health care treatment being selected by the user via the client system from a plurality of health care treatments; and
wherein, upon receiving the indication of the selected health care treatment, the network service is operable to automatically transmit, over the network to the client system, the statistics to the client system for rendering a user interface implemented at the client system, the user interface comprising:
a timeline for the selected health care treatment, the timeline displaying an average duration for each of an evaluation phase, a treatment phase, and a follow-up phase, the timeline determined from at least one data set of the plurality of data sets; and
an outline of health care services associated with the evaluation phase, the treatment phase, and the follow-up phase, the outline displaying the statistics for each of the health care services.

11. The apparatus of claim 10, wherein the user interface further comprises an average total cost and an estimated out-of-pocket cost of the selected health care treatment.

12. The apparatus of claim 11, wherein the average total cost and the estimated out-of-pocket cost of the selected health care treatment are calculated by the logic subsystem based at least in part on a type of health care facility providing the health care treatment.

13. The apparatus of claim 11, wherein the average total cost and the estimated out-of-pocket cost of the selected health care treatment are calculated by the logic subsystem by summing the cost of each health care service within the selected health care treatment.

14. The apparatus of claim 10, wherein the statistics further include a frequency of each health care treatment within an episode grouping, wherein each treatment comprises at least one health care service.

15. The apparatus of claim 10, wherein the statistics further include a frequency of patients receiving a health care service within a health care treatment.

16. The apparatus of claim 14, wherein the outline of the health care services does not include a health care service for which a frequency of patients receiving the health care service is below a threshold.

17. The apparatus of claim 16, wherein the threshold comprises 5%.

18. The apparatus of claim 10, wherein the statistics further include an average time that a health care service occurs after the beginning of a health care treatment.

19. The apparatus of claim 18, wherein the timeline is generated based on the statistics.

20. The system of claim 1, wherein the logic subsystem is further configured to calculate the statistics based on each of the plurality of data sets while each of the plurality of data sets is loaded in the volatile memory according to how each of the plurality of data sets was partitioned from the raw medical claims data, and wherein calculating the statistics includes calculating the frequency of patients receiving the health care service based on a second data set of the plurality of data sets partitioned by one or more episode groupings relating to the health care service.

* * * * *